US007070811B2

(12) United States Patent
Murphy et al.

(10) Patent No.: US 7,070,811 B2
(45) Date of Patent: *Jul. 4, 2006

(54) DIRECTLY COMPRESSIBLE FORMULATIONS OF AZITHROMYCIN

(75) Inventors: Brendan Murphy, Quaker Hill, CT (US); Steven W. Collier, Oakland, CA (US); Ernest Quan, East Lyme, CT (US); Barbara A. Johnson, Niantic, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/190,393

(22) Filed: Jul. 26, 2005

(65) Prior Publication Data

US 2005/0287209 A1    Dec. 29, 2005

Related U.S. Application Data

(63) Continuation of application No. 10/327,459, filed on Dec. 20, 2002.

(60) Provisional application No. 60/343,480, filed on Dec. 21, 2001.

(51) Int. Cl.
*A61K 9/14* (2006.01)
*A61K 31/70* (2006.01)

(52) U.S. Cl. ............... 424/489; 424/464; 424/465; 514/29; 536/7.4

(58) Field of Classification Search ............ 424/464, 424/465, 489; 514/29; 536/7.4
See application file for complete search history.

(56) References Cited

U.S. PATENT DOCUMENTS

| | | | | |
|---|---|---|---|---|
| 4,474,768 | A | 10/1984 | Bright | 424/180 |
| 4,963,531 | A | 10/1990 | Remington | 514/29 |
| 5,047,246 | A | 9/1991 | Gallian et al. | 424/464 |
| 5,605,889 | A | 2/1997 | Curatolo et al. | 514/29 |
| 5,633,006 | A | 5/1997 | Catania et al. | 424/441 |
| 6,068,859 | A | 5/2000 | Curatolo et al. | 424/490 |
| 6,245,903 | B1 | 6/2001 | Karimian et al. | 536/7.4 |
| 6,268,489 | B1 | 7/2001 | Allen et al. | 536/7.4 |
| 6,339,063 | B1 | 1/2002 | Kropp et al. | 514/29 |
| 6,365,574 | B1 | 4/2002 | Singer et al. | 514/29 |

FOREIGN PATENT DOCUMENTS

| | | |
|---|---|---|
| EP | 0298650 | 2/1992 |
| EP | 0758549 | 2/1997 |
| EP | 1103558 | 6/2003 |
| IL | 0119866 | 12/1999 |
| WO | WO9530422 | 11/1995 |
| WO | WO9835681 | 8/1998 |
| WO | WO9912552 | 3/1999 |
| WO | WO0057886 | 10/2000 |
| WO | WO0209640 | 2/2002 |
| WO | WO02094843 | 11/2002 |

OTHER PUBLICATIONS

Sheth, B, Bandelin, Fred, Shangraw, Ralph, Compressed Tablets in *Pharmaceutical Dosage Forms: Tablets*, vol. 1, Lieberman, Herbert A. and Lachman, Leon, eds., Marcel Dekker, Inc., New York 1980, pp. 109-185.
Rawle, Alan, "Basic Principles of Particle Size Analysis" Technical Paper from Malvern Instruments, pp. 1-8.
Hiestand, H.E.N. and Smith, D.P., "Indices of Tableting Performance", Powder Technology, 38 (1994) 145-159.
*Tableting Specification Manual*, 4th Edition, AphA, Washing DC (1995) Figure 25, p. 51.
Watt, Peter Ridgway, *Tablet Machine Instrumentation in Pharmaceutics: Principles and Practice*, Halsted Press, John Wiley & sons, New York (1988) pp. 19-25; 429, 430, 434.
Banker, Gilbert S., "Tablets and Tablet Product Design", *Sprowls' American Pharmacy*, Seventh Edition, Dittert, Lewis W. ed., J.B. Lippincott Company, Philadelphia (1974) pp. 379-381.
Hiestand, E.N. and Wilcox, C.J., Some Measurements of Friction in Simple Powder Beds J. Pharm. Sci. 57 (1968) 1421-1427 (information on internal angle of friction).

(Continued)

*Primary Examiner*—Elli Peselev
(74) *Attorney, Agent, or Firm*—Gregg C. Benson; B. Timothy Creagan; Lance Y. Liu

(57) ABSTRACT

The present invention relates to a dry blend, used for forming azithromycin tablets by direct compression, comprising non-dihydrate azithromycin and at least one pharmaceutically acceptable excipient.

This invention also relates to an azithromycin tablet comprising non-dihydrate azithromycin and at least one pharmaceutically acceptable excipient. Preferably, the azithromycin tablet is formed by directly compressing the dry blend, of the present invention, to form said azithromycin tablet.

Preferably, the azithromycin tablet, of the present invention, contains a dosage of 250 mgA, 500 mgA or 600 mgA of azithromycin.

This invention further relates to an azithromycin tablet which is produced by forming a dry blend of a non-granulated azithromycin form A and at least one pharmaceutically acceptable excipient. The azithromycin tablet is then formed by directly compressing the dry blend.

36 Claims, 1 Drawing Sheet

OTHER PUBLICATIONS

Wells, James I., *Pharmaceutical Preformulation: The Physicochemical Properties of Drug Substances*, Halsted Press, John Wiley & Sons, New York (1988) pp. 209-214.

*Handbook of Powder Science and Technology*, Fayed, M.E. and Otten, L., eds., Van Nostrand Reinhold Co., New York (1984) pp. 262, 396-407.

Tan, S.B. and Newton, J.M., "Powder flowability as an indication of capsule filling performance", International Journal of Pharmaceutics, 61, (1990) 145-155.

Carr, Ralph L., Jr., "Evaluating Flow Properties of Solids" Chemical Engineering, Jan. 18, 1965, 163-168 (1965).

Cohard, C., Chulia, D., Gonthier, Y. and Verain, A., "A Correlation Between Flowability and Tapping Variation Rates of Powders", Int. J. Pharm. Tech. & Prod. Mfr., 6 (3) 10-16 (1985).

Sadek, H.M., Olsen, J.L., Smith, H.L. and Onay, S. "A systematic approach to gildant selection" Pharmaceutical Technology, Feb. 1982, 42-62.

Dawoodbhai, Shabbir and Rhodes, Christopher T., "Pharmaceutical and Cosmetic Uses of Talc", Drug Development and Industrial Pharmacy, 16(16), 2409-2429 (1990).

Dawoodbhai, Shabbir and Rhodes, Christopher T., "Glidants and Lubricant Properties of Several Types of Talcs", Drug Development and Industrial Pharmacy, 13(13), 2441-2467(1987).

Chang, Rong-Kun, Leonzlo, Michael and Hussain, Munir A., "Effect of Colloidal Silicon Dioxide on Flowing and Tableting Properties of an Experimental, Crosslinked Polyalkylammonium Polymer", Pharmaceutical Development and Techlology, 4(2), 285-289 (1999).

H. Kibbe, ed., *Handbook of Pharmaceutical Excipients*, Third Edition, American Pharmaceutical Association, 2000 (Colloidal Silicon Dioxode, Croscarmellos Sodium, Lactose, monohydrate spray-dried, Magnesium Stearate, Microcrystalline Cellulose, Sodium Lauryl Sulfate, Talc).

Chinese language document cited by the Taiwanese Associate, p. 341.

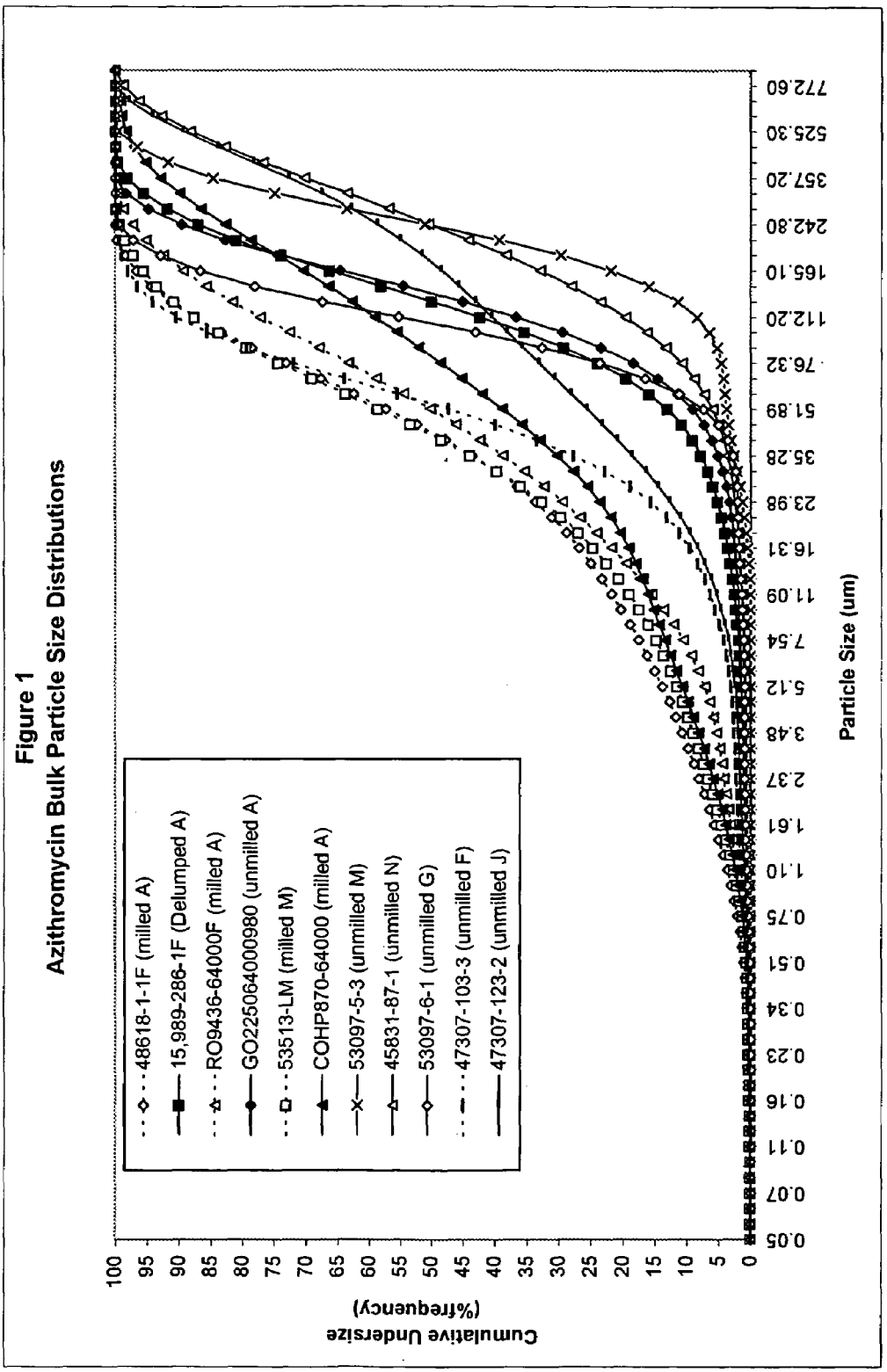

DIRECTLY COMPRESSIBLE FORMULATIONS OF AZITHROMYCIN

This application is a continuation of U.S. Ser. No. 10/327,459, filed Dec. 20, 2002, which is a non provisional of Provisional Applications 60/343,480, filed Dec. 21, 2001.

BACKGROUND OF THE INVENTION

Direct compression is a tableting process in which tablets are compressed directly from powder blends containing an active ingredient. In direct compression, all the ingredients required for tableting, including the active ingredient and processing aids, are incorporated into a free flowing blend which is then tableted. The active ingredient, excipients, and other substances are blended and then compressed into tablets. Tablets are typically formed by pressure being applied to a material in a tablet press.

There are a number of tablet presses, each varying in productivity and design but similar in basic function and operation. All compress a tablet formulation within a die cavity by pressure exerted between two steel punches, a lower punch and an upper punch.

Pharmaceutical manufacturers prefer the use of direct compression, over wet and dry granulation processes, because of its shorter processing times and cost advantages. However, direct compression is generally limited to those situations in which the active ingredient has physical characteristics suitable for forming pharmaceutically acceptable tablets.

Some active ingredients, which are generally unsuitable for direct compression, can be formed into a directly compressible formulation by incorporating one or more excipients before compressing. The addition of excipients to the formulation, however, will increase the tablet size of the final product. As tablet size must be within certain parameters to function as a suitable dosage form, there is a limit beyond which increasing tablet size to accommodate increasing amounts of excipients to enhance compactability is not practical. As a result, manufacturers are often limited to using the direct compression method for formulations containing a low dose of the active ingredient per compressed tablet such that the formulation may accommodate sufficient levels of excipient to make direct compression practical.

In the development of pharmaceutical dosage forms, it is important to balance several different objectives. Preparation of a pharmaceutical dosage form should be economical. Also, the dosage form should be easy to swallow. Further, smaller dosage forms are more acceptable to patients and result in improved patient compliance.

It is known that, to form a tablet from a given formulation, the formulation must have good flow properties for precise volumetric feeding of the material to the die cavity and suitable compressibility, compactability, and ejection properties to form a tablet. The flow properties of powders are critical for efficient tableting operation. The ability of the material to flow freely into the die is important to ensure that there is uniform filling of the die and a continuous movement of the material from its source. Poor flow properties of the material will affect the weight, hardness and friability of the tablets. Good flow of powders, to be compressed, is necessary to assure efficient mixing and acceptable weight uniformity for the compressed tablets.

Azithromycin, which is also named 9-deoxo-9a-aza-9a-methyl-9a-homoerythromycin A, generally, is not considered to be amenable to the production of directly compressible tablets of azithromycin formulations.

It would be desirable to develop an azithromycin formulation that is amenable to direct compression and that produces tablets having acceptable hardness and friability.

SUMMARY OF THE INVENTION

The present invention relates to a dry blend, used for forming azithromycin tablets by direct compression, comprising non-dihydrate azithromycin and at least one pharmaceutically acceptable excipient.

This invention also relates to an azithromycin tablet comprising non-dihydrate azithromycin and at least one pharmaceutically acceptable excipient. Preferably, the azithromycin tablet is formed by directly compressing the dry blend, of the present invention, to form said azithromycin tablet.

Preferably, the azithromycin tablet, of the present invention, contains a dosage of 250 mgA, 500 mgA or 600 mgA of azithromycin.

This invention further relates to an azithromycin tablet which is produced by forming a dry blend of a non-granulated azithromycin form A and at least one pharmaceutically acceptable excipient. The azithromycin tablet is then formed by directly compressing the dry blend.

BRIEF DESCRIPTION OF THE DRAWINGS

FIG. 1 is a plot of the bulk particle size distribution of azithromycin for azithromycin lots 1 through 11 by light scattering analysis (Malvern Mastersizer S, Malvern Instruments, Worcestershire, UK).

As used in FIG. 1:

The -△- symbol represents the particle size distribution of bulk lot 1

The -x- symbol represents the particle size distribution of bulk lot 2

The -♦- symbol represents the particle size distribution of bulk lot 3

The -◇- symbol represents the particle size distribution of bulk lot 4

The -■- symbol represents the particle size distribution of bulk lot 5

The -▲- symbol represents the particle size distribution of bulk lot 6

The ... ◇ ... symbol represents the particle size distribution of bulk lot 7

The ... △ ... symbol represents the particle size distribution of bulk lot 8

The ... □ ... symbol represents the particle size distribution of bulk lot 9

The ... ○ ... symbol represents the particle size distribution of bulk lot 10

The -●- symbol represents the particle size distribution of bulk lot 11

DETAILED DESCRIPTION

In the specification and claims that follow, reference will be made to a number of terms which shall be defined to have the following meaning.

The term "dry blend", as used herein, means a generally homogeneous mixture of two or more materials in particle form. The particles may be in powdered form or, alternatively, larger aggregated or agglomerated particles.

The term "azithromycin" as used herein includes all crystalline and amorphous forms of azithromycin, including all polymorphs, isomorphs, clathrates, salts, solvates and hydrates of azithromycin, unless specifically stated. Azithromycin forms include the dihydrate form and various non-dihydrate forms.

The stable dihydrate of azithromycin, which is essentially non-hygroscopic under conditions of relative humidity conducive to formulation of azithromycin and is disclosed in U.S. Pat. No. 6,268,489, is designated herein as "form A". The form is a crystalline dihydrate, prepared by crystallization from tetrahydrofuran and an aliphatic ($C_5$–$C_7$) hydrocarbon in the presence of at least two molar equivalents of water.

"Non-dihydrate azithromycin" means all amorphous and crystalline forms of azithromycin including all polymorphs, isomorphs, clathrates, salts, solvates and hydrates of azithromycin other than form A, the dihydrate form of azithromycin (azithromycin dihydrate).

Non-dihydrate azithromycin includes a hygroscopic hydrate of azithromycin, as disclosed in U.S. Pat. No. 4,474,768, which is designated herein as "form B".

Azithromycin may be present in several alternate crystalline non-dihydrate forms, including forms D, E, F, G, H, J, M, N, O, P, Q and R, which are disclosed in U.S. patent application Ser. No. 10/152,106, filed 21 May 2002, the teachings of which are incorporated herein, by reference, in their entirety.

Both Family I and Family II isomorphs are hydrates and/or solvates of azithromycin. The solvent molecules in the cavities have a tendency to exchange between solvent and water under specific conditions. Therefore, the solvent/water content of the isomorphs may vary to a certain extent. Forms B, F, G, H, J, M, N, O, and P belong to Family I azithromycin and belong to a monoclinic $P2_1$ space group with cell dimensions of a=16.3±0.3 ∈, b=16.2±0.3 ∈, c=18.4±0.3 ∈ and beta=109±2°. Forms D, E and R belong to Family II azithromycin and belong to an orthorhombic $P2_1 2_1 2_1$ space group with cell dimensions of a=8.9±0.4 ∈, b=12.3±0.5 ∈ and c=45.8±0.5 ∈. Form Q is distinct from Families I and II.

Form D azithromycin is of the formula $C_{38}H_{72}N_2O_{12}.H_2O.C_6H_{12}$ in its single crystal structure, being azithromycin monohydrate monocyclohexane solvate. Form D is further characterized as containing 2–6% water and 3–12% cyclohexane by weight in powder samples. From single crystal data, the calculated water and cyclohexane content of form D is 2.1 and 9.9%, respectively.

Form E azithromycin is of the formula $C_{38}H_{72}N_2O_{12}.H_2O.C_4H_8O$ being azithromycin monohydrate mono-tetrahydrofuran solvate. Form E is a monohydrate and mono-THF solvate by single crystal analysis.

Form G azithromycin is of the formula $C_{38}H_{72}N_2O_{12}.1.5H_2O$ in the single crystal structure, being azithromycin sesquihydrate. Form G is further characterized as containing 2.5–6% water and <1% organic solvent(s) by weight in powder samples. The single crystal structure of form G consists of two azithromycin molecules and three water molecules per asymmetric unit. This corresponds to a sesquihydrate with a theoretical water content of 3.5%. The water content of powder samples of form G ranges from about 2.5 to about 6%. The total residual organic solvent is less than 1% of the corresponding solvent used for crystallization.

Form H azithromycin is of the formula $C_{38}H_{72}N_2O_{12}.H_2O.0.5C_3H_8O_2$ being azithromycin monohydrate hemi-1,2 propanediol solvate. Form H is a monohydrate/hemi-propylene glycol solvate of azithromycin free base.

Form J azithromycin is of the formula $C_{38}H_{72}N_2O_{12}.H_2O.0.5C_3H_7OH$ in the single crystal structure, being azithromycin monohydrate hemi-n-propanol solvate. Form J is further characterized as containing 2–5% water and 1–5% 1-propanol by weight in powder samples. The calculated solvent content is about 3.8% n-propanol and about 2.3% water.

Form M azithromycin is of the formula $C_{38}H_{72}N_2O_{12}.H_2O.0.5C_3H_7OH$, being azithromycin monohydrate hemi-isopropanol solvate. Form M is further characterized as containing 2–5% water and 1–4% 2-propanol by weight in powder samples. The single crystal structure of form M would be a monohydrate/hemi-isopropranolate.

Form N azithromycin is a mixture of isomorphs of Family I. The mixture may contain variable percentages of isomorphs, F, G, H, J, M and others, and variable amounts of water and organic solvents, such as ethanol, isopropanol, n-propanol, propylene glycol, acetone, acetonitrile, butanol, pentanol, etc. The weight percent of water can range from 1–5.3% and the total weight percent of organic solvents can be 2–5% with each solvent content of 0.5 to 4%.

Form O azithromycin is of the formula $C_{38}H_{72}N_2O_{12}.0.5H_2O.0.5C_4H_9OH$, being a hemihydrate hemi-n-butanol solvate of azithromycin free base by single crystal structural data.

Form P azithromycin is of the formula $C_{38}H_{72}N_2O_{12}.H_2O.0.5C_5H_{12}O$ being azithromycin monohydrate hemi-n-pentanol solvate.

Form Q azithromycin is of the formula $C_{38}H_{72}N_2O_{12}.H_2O.0.5C_4H_8O$ being azithromycin monohydrate hemi-tetrahydrofuran solvate. It contains about 4% water and about 4.5% THF.

Form R azithromycin is of the formula $C_{38}H_{72}N_2O_{12}.H_2O.C_5H_{12}O$ being azithromycin monohydrate monomethyl tert-butyl ether solvate. Form R has a theoretical water content of 2.1 weight % and a theoretical methyl tert-butyl ether content of 10.3 weight %.

Form F azithromycin is of the formula $C_{38}H_{72}N_2O_{12}.H_2O.0.5C_2H_5OH$ in the single crystal structure, being azithromycin monohydrate hemi-ethanol solvate. Form F is further characterized as containing 2–5% water and 1–4% ethanol by weight in powder samples.

The single crystal of form F is crystallized in a monoclinic space group, $P2_1$, with the asymmetric unit containing two azithromycins, two waters, and one ethanol, as a monohydrate/hemi-ethanolate. It is isomorphic to all Family I azithromycin crystalline forms. The theoretical water and ethanol contents are 2.3 and 2.9%, respectively.

The term "non-granulated" azithromycin, as used herein, means that the azithromycin is not dry granulated, such as by slugging or roller compaction, or wet granulated.

"Bulk azithromcyin", as used herein, means azithromycin particles without added excipients.

The term "pharmaceutically acceptable" means that which is generally safe, non-toxic and neither biologically nor otherwise undesirable and includes that which are acceptable for veterinary use as well as human pharmaceutical use.

The phrase "directly compressible formulation" means a formulation which can be compressed into a pharmaceutically acceptable tablet without a prior granulation step.

The term "compressibility" means the degree to which a formulation decreases in volume when air is removed.

The term "compactibility" means the ease with which a formulation is compressed into tablets possessing acceptable hardness properties.

The term "free flowing" as used herein means the ability of material to flow without mechanical agitation on standard tableting equipment utilizing gravity to induce flow, such as an F-press. Good flowing materials result in dosage forms with good weight uniformity as evidenced by low relative standard deviation (% RSD) or coefficient of variation (% CV) of dosage form weight.

The term "fines" as used herein refers to particles with a diameter of less than about 44 microns, as measured by the Malvern method.

The term "F-press" as used herein refers to a MANESTY F-PRESS (Manesty Machines Ltd., UK).

The term "mgA" refers to milligrams of the free base of azithromycin.

In the method of the present invention, the azithromycin used may be milled or unmilled bulk drug.

The dry blend, of the present invention, is used to produce non-dihydrate azithromycin tablets by direct compression. Typically, the dry blend contains from about 1% to about 80% of non-dihydrate azithromycin. Preferably, the azithromycin, in the dry blend, is non-granulated.

It is also preferred that the azithromycin in the dry blend comprise a form of non-dihydrate azithromycin selected from forms B, D, E, F, G, H, J, M, N, O, P, Q, R, or mixtures thereof.

In addition to the non-dihydrate azithromycin, the dry blend of the present invention, also includes at least one pharmaceutically acceptable suitable excipient. The excipients may include processing aids that improve the direct compression tablet-forming properties of the dry blend.

In one embodiment of the present invention, the dry blend is suitable for use in forming azithromycin tablets through gravity-fed, direct compression tableting.

To be suitable for direct compression on a gravity fed tableting press, particularly at higher azithromycin loadings, such as 45% or more, the particle size profile of azithromycin, is critical. As azithromycin loading increases, the fines in the bulk azithromycin tend to further degrade the flow properties of the dry blend as they constitute a higher percentage of the total particles within the dry blend. Therefore, it is necessary to reduce the amount of azithromycin fines within the dry blend to obtain acceptable flow on a gravity fed tableting press and make a tablet having acceptable friability.

By "gravity fed tableting press" it is meant that a pharmaceutical formulation is not force fed into a die, and that the flow of the pharmaceutical formulation is induced by gravity. An example of a gravity fed tableting press is the Manesty F-press.

In this embodiment of the present invention, the particle size distribution was determined using a Malvern Mastersizer S (Malvern Instruments, Worcestershire, UK) with a MS-1-Small Volume Sample Dispersion Unit. This unit allowed for particle size analysis through a wet sample dispersion step and subsequent particle size measurements using laser diffraction.

In this embodiment of the present invention, to achieve suitable flow properties for the dry blend, particularly at higher azithromycin loadings, typically, less than about 20% of the azithromycin particles, by volume, in the dry blend, should have a diameter of 44 µm or less. Preferably, less than about 14% of the azithromycin particles should have a diameter of 44 µm or less.

Likewise, in the present dry blend, it is preferred that less than about 27% of the azithromycin particles should have a diameter of 74 µm or less.

Further, in the present dry blend, it is preferred that less than about 60% of the azithromycin particles should have a diameter of 105 µm or less. More preferably less than about 50% of the azithromycin particles should have a diameter of 105 µm or less.

Even more preferably, less than about 6% of the azithromycin particles should have a diameter of 16 µm or less.

In a more preferred embodiment of the present invention, the dry blend contains less than about 6% of the azithromycin particles, by volume, with a diameter of about 16 µm or less, and less than about 20% of the azithromycin particles, by volume, with a diameter of about 44 µm or less. Even more preferably, less than about 14% of the azithromycin particles should have a diameter of 44 µm or less.

In an even more preferred embodiment, the dry blend contains less than about 6% of the azithromycin particles, by volume, with a diameter of about 16 µm, or less, less than about 20% of the azithromycin particles, by volume, with a diameter of about 44 µm, or less, and less than about 27% of the azithromycin particles, by volume, with a diameter of about 74 µm or less. Even more preferably, less than about 14% of the azithromycin particles should have a diameter of 44 µm or less.

In yet an even more preferred embodiment, the dry blend contains less than about 6% of the azithromycin particles, by volume, with a diameter of about 16 µm, or less, less than about 20% of the azithromycin particles, by volume, with a diameter of about 44 µm, or less, less than about 27% of the azithromycin particles, by volume, with a diameter of about 74 µm, or less, and less than about 60% of the azithromycin particles, by volume, with a diameter of about 105 µm or less. Even more preferably, less than about 14% of the azithromycin particles should have a diameter of 44 µm, or less, and less than about 50% of the azithromycin particles should have a diameter of 105 µm or less.

The flow properties of a dry blend may be evaluated by a number of methods known in the art. One way of characterizing formulation properties of a powdered material is by bulk density measurements. A simple method to provide a description of flow characteristics by bulk density measurement is Carr's Compressibility Index (Carr's Index).

Carr's Compressibility Index is a simple test to evaluate flowability by comparing both the initial and final (tapped) densities and the rate of packing down. A useful empirical guide to flow is given by Carr's compressibility index:

$$\text{Compressibility Index}(\%) = [(\text{tapped density} - \text{initial density})/\text{tapped density}] \times 100$$

In the present invention, it was found that the Carr's Compressibility Index of the dry blend provided a good indication of the flow characteristics and thus, the suitability for using the dry blend to prepare tablets through gravity-fed, direct compression tableting. Generally, it was observed that formulations with Carr's Compressibility Index values of less than about 34% resulted in acceptable flow and tabletability on an F-press, whereas formulations with values of 34%, or more, resulted in poor flow and an inability to form suitable tablets on an F-press. Therefore, in the present invention, the dry blend should have a Carr's Compressibility Index less than about 34%, more preferably less than about 31%, and even more preferably less than about 28%.

Another measurement of particle flow is the internal angle of friction that may be determined by shear cell experiments.

The primary difference in the flow behavior of liquids and powders is in their internal friction. The lack of internal friction of liquids allows them to form level surfaces at rest, while internal friction in powders allows the formation of heaps or other non-level surfaces.

Internal friction of powders is typically characterized using a shear cell, which is a device that places a powder sample under known physical stress conditions and measures its response to those stresses, as disclosed in "Some Measurements of Friction in Simple Powder Beds", Heistand, E. N. and Wilcox, C. J. (J. Pharm. Sci. 57 (1968) 1421), incorporated herein by reference. The response is reported as an angle of internal friction. This parameter is a characteristic of the powders measured and varies between materials. The lower the value of the angle of internal friction, the better flowing the powder is. This parameter may be used as a predictor of tablet weight variation during tableting operations, since the powder fill weight, and therefore the tablet weight, is dependent on the ability of the powder to quickly flow into the tableting die. In the present invention, dry blends, suitable for use in the preparation of tablets by direct compression, had angles of internal friction of less than about 34°, and more preferably less than about 31°.

Even more preferably, dry blends of the present invention have a Carr's Compressibility Index of less than about 34% and an internal angle of friction of less than about 34°.

Most preferably, dry blends of the present invention have a Carr's Compressibility Index of less than about 28% and an internal angle of friction of less than about 31°.

A dry blend, having properties within the aforementioned ranges, may be achieved by methods including, but not limited to, providing suitable excipients, by increasing particle size, or by modifying processing conditions. Typically, addition of excipients provides a means to modify the flow profile of a low dose pharmaceutical formulation, as commercially available excipients have good flow properties. For dry blends, having higher azithromycin loadings, Carr's Compressibility Index and/or internal angles of friction with the aforementioned ranges may be achieved by obtaining the azithromycin particle size distribution discussed above.

Accordingly, the particle size profile of the azithromycin should be evaluated, and if necessary, the azithromycin should be processed to achieve the particle size profile.

To produce azithromycin particles having the desired particle size distribution, the bulk azithromycin may be further processed by methods including, but not limited to, 1) milling 2) screening 3) recrystallization and 4) granulation, including dry and wet granulation. The aforementioned further processing methods may be used alone or in combination.

Milling involves subjecting the drug to a shear force such that the particle size of the drug is reduced. The milling may be an aggressive process where the particle size is reduced significantly, or it may be a non-aggressive process where the particle size is not reduced significantly, but merely done to delump or break up larger clumps of drug formed in the bulk drug.

In the pharmaceutical industry, milling is often used to reduce the particle size of solid materials. Many types of mills are available including pin mills, hammer mills and jet mills. One of the most commonly used types of mill is the hammer mill. The hammer mill utilizes a high-speed rotor to which a number of fixed or swinging hammers are attached. The hammers can be attached such that either the knife face or the hammer face contacts the material. As material is fed into the mill, it impacts on the rotating hammers and breaks up into smaller particles. A screen is located below the hammers, which allows the smaller particles to pass through the openings in the screen. Larger particles are retained in the mill and continue to be broken up by the hammers until the azithromycin particles are fine enough to flow through the screen.

The azithromycin particles may optionally be screened. In screening, bulk drug is placed through a mesh screen or series of mesh screens to obtain the desired particle size for the bulk drug.

Several methods are known for increasing the particle size of drugs, including, but not limited to, granulation and recrystallization. Wet granulation, for example, involves the use of a granulating liquid that causes the azithromycin particles to agglomerate and thus increase the particle size. Suitable wet granulation methods for the preparation of azithromycin particles are disclosed in copending U.S. Provisional Application Ser. No. 60/343,469, titled "Methods for Wet Granulating Azithromycin", filed Dec. 21, 2001 and in copending International. application Ser. Number 10/327,383 titled "Methods for Wet Granulating Azithromycin". Suitable methods for dry granulating azithromycin particles are disclosed in copending U.S. Provisional Application Ser. No. 60/354,041, titled "Dry Granulated Formulations of Azithromycin", filed Feb. 1, 2002.

In the present invention, wet granulation of the bulk drug without the use of additional excipients may be used to increase the particle size of the material Recrystallization involves dissolving a bulk drug and allowing it to reform as new crystals which are adequate in particle size for the use in an azithromycin direct compression tablet.

Another method to increase the particle size is to sieve the bulk drug to remove the smaller particles.

While it was found that the azithromycin particle size distribution was important for achieving acceptable flow properties on gravity fed tableting equipment, dry blends with lower azithromycin loadings or with an undesirable amount of fines may still be directly compressed to form tablets by adjusting the processing conditions, equipment and/or excipients as necessary. For example, a dry blend with a higher amount of fines may be tableted, by direct compression, through using forced fed tableting equipment. Methods of assisting flow, or force feeding, are well known in the art.

Thus, in an alternative embodiment of the present invention, a non-dihydrate azithromycin dry blend can be mechanically processed in a manner to compensate for poor flow properties. For example, the material may be introduced into the die using a mechanical force feeder. A mechanical force feeder might be used when poor weight control is obtained using a pharmaceutical formulation. Further, the flow properties of a dry blend may also be modified by decreasing the percentage of bulk azithromycin in the dry blend.

The amount of azithromycin and of the additional excipients and processing aids may be varied provided suitable direct compressibility properties of the pharmaceutical formulation are achieved, as defined by flow measurements such as Carr's Compressibility Index and internal angle of friction as described herein.

Any additional excipients, such as diluent or dry binder should preferably have good flow characteristics and compactibility. Excipients having good flow properties are readily available.

In the dry blend, of the present invention, excipients suitable for use in direct compression include, but are not limited to, binders, diluents, disintegrants, lubricants, fillers, carriers, and the like.

Binders are used to impart cohesive qualities to a tablet formulation, and thus ensure that a tablet remains intact after compaction. Suitable binder materials include, but are not limited to, microcrystalline cellulose, gelatin, sugars (including sucrose, glucose, dextrose and maltodextrin), polyethylene glycol, waxes, natural and synthetic gums, polyvinylpyrrolidone, cellulosic polymers (including hydroxypropyl cellulose, hydroxypropyl methylcellulose, methyl cellulose, hydroxyethyl cellulose, and the like).

Lubricants can be employed herein in the manufacture of certain dosage forms, and will usually be employed when producing tablets. In the present invention, a lubricant is added just before the tableting step, and is mixed with the formulation for a minimum period of time to obtain good dispersal. The lubricant employed in a composition of the present invention may be one or more compounds. Examples of suitable lubricants include, but are not limited to, magnesium stearate, calcium stearate, zinc stearate, stearic acid, talc, glyceryl behenate, polyethylene glycol, polyethylene oxide polymers (for example, available under the registered trademarks of Carbowax™ for polyethylene glycol and Polyox™ for polyethylene oxide from Dow Chemical Company, Midland, Mich.), sodium lauryl sulfate, magnesium lauryl sulfate, sodium oleate, sodium stearyl fumarate, DL-leucine, colloidal silica, and others as known in the art. Preferred lubricants are magnesium stearate, calcium stearate, zinc stearate and mixtures of magnesium stearate with sodium lauryl sulfate. Lubricants may comprise from about 0.25% to about 10% of the tablet weight, more preferably from about 0.5% to about 3%.

Disintegrants are used to facilitate tablet disintegration or "breakup" after administration, and are generally starches, clays, celluloses, algins, gums or crosslinked polymers. Suitable disintegrants include, but are not limited to, crosslinked polyvinylpyrrolidone (PVP-XL), sodium starch glycolate, and croscarmellose sodium. If desired, the pharmaceutical formulation may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, sodium lauryl sulfate, dioctyl sodium sulfosuccinate, polyoxyethylene sorbitan fatty acid esters, etc.

The diluent employed in a composition of the present invention may be one or more compounds which are capable of providing compactibility and good flow. A variety of materials may be used as fillers or diluents. Suitable diluents or fillers include, but are not limited to, lactose (monohydrate, spray-dried monohydrate, anhydrous and the like), sucrose, dextrose, mannitol, sorbitol, starch, cellulose (e.g. microcrystalline cellulose; Avicel®, FMC Biopolymer, Philadelphia, Pa.), dihydrated or anhydrous dibasic calcium phosphate, calcium carbonate, calcium sulfate, and others as known in the art. More preferably, free-flowing diluents which can improve blend flow are: spray-dried lactose monohydrate (such as 316 Fast Flo®, Foremost Farms, Baraboo, Wis. and Phamatose® DCL 11, DMV International Pharma, Veghel, The Netherlands), agglomerated free-flowing lactose monohydrate (such as Tablettose®, Meggle GMBH, Wasserburg, Germany), granulated lactose monohydrate (such as Pharmatose® DCL 15, DMV International Pharma, Veghel, The Netherlands), roller dried lactose monohydrate (such as Pharmatose® DCL 21, DMV International Pharma, Veghel, The Netherlands), direct compression lactose, anhydrous (such as Pharmatose® DCL 40, DMV International Pharma, Veghel, The Netherlands and Anhydrous DT Lactose, Quest International Inc., Hoffman Estates, Ill.), spray-dried lactose with microcrystalline cellulose (MicroLac® 100, Meggle GMBH, Wasserburg, Germany), spray-dried lactose with cellulose (Cellactose®, Meggle GMBH, Wasserburg, Germany), direct compression sucrose (such as Sugartab®, Penwest Pharmaceuticals Co., Patterson, N.Y. and Nu-Tab®, DMV International Pharma, Veghel, The Netherlands), co-crystallized sucrose and modified dextrins (Di-Pac®, DominoSpecialty Ingredients, Baltimore, Md.), spray-dried dextrates (Emdex®, Penwest Pharmaceuticals Co., Patterson, N.Y.), coarse dextrose (such as Cerelose® Coarse Dextrose 2037, Corn Products International, Inc., Westchester, Ill.), agglomerated dextrose (such as Unidex® 2034, Corn Products International, Inc., Westchester, Ill.), spray-dried maltodextrin (such as Maltrin® M 510, Grain Processing Corp., Muscatine, Iowa), fine granular maltodextrin (such as Maltrin® M 150, Grain Processing Corp., Muscatine, Iowa), spray-dried maltose (Advantose™ 100 Maltose Powder, SPI Pharma, New Castle, Del.), spray-dried mannitol (such as Mannogem™ EZ Spray Dried Mannitol, SPI Pharma, New Castle, Del. and Parteck™ M, EM Industries, Inc., Hawthorne, N.Y.), granular mannitol (such as Mannitol Granular 2080, SPI Pharma, New Castle, Del. and Mannitol Granular, SPI Pharma, New Castle, Del.), spray-dried sorbitol (such as Parteck™ SI [Sorbitol Instant™], EM Industries, Inc., Hawthorne, N.Y.), coarse sorbitol (such as grades 834, 2016 and 1162 Crystalline Sorbitol, SPI Pharma, New Castle, Del.), direct compression fructose co-dried with starch (Advantose™ FS95 Fructose, SPI Pharma, New Castle, Del.), pregelatinized corn starch (such as Spress® B820, Grain Processing Corp., Muscatine, Iowa and Starch 1500®, Colorcon Inc., West Point, Pa.), high density microcrystalline cellulose (such as Avicel® PH-302, FMC Biopolymer, Philadelphia, Pa., Pharmacel® 200, DMV International Pharma, Veghel, The Netherlands and Emcocel® HD90, Penwest Pharmaceuticals Co., Patterson, N.Y.), direct compression microcrystalline cellulose (such as Avicel™ PH-200, FMC Biopolymer, Philadelphia, Pa., Pharmacel® 102, DMV International Pharma, Veghel, The Netherlands and Emcocel® 90M and Emcocel® LP200, Penwest Pharmaceuticals Co., Patterson, N.Y.), direct compression silicified microcrystalline cellulose (such as Prosolv SMCC™ 90, Penwest Pharmaceuticals Co., Patterson, N.Y.), free-flowing grades of dibasic calcium phosphate, dihydrate (such as Emcompress®, Penwest Pharmaceuticals Co., Patterson, N.Y. and Di-Tab®, Rhodia Inc, Cranbury, N.J.) and free-flowing grades of dibasic calcium phosphate, anhydrous (such as Anhydrous Emcompress®, Penwest Pharmaceuticals Co., Patterson, N.Y. and A-Tab®, Rhodia Inc, Cranbury, N.J.). Most preferred free-flowing diluents are spray-dried lactose and free-flowing lactose monohydrate grades, high density and direct compression grades of microcrystalline cellulose and silicified microcrystalline cellulose, spray-dried dextrates, spray-dried and granular mannitol, spray-dried and coarse sorbitol and free-flowing grades of dibasic calcium phosphate, dihydrate.

In the present invention, it is more preferred that these diluents be used to reduce the Carr's index and to reduce the angle of internal friction for azithromycin formulations, particularly in dry blends containing an azithromycin drug loading of about 30% or more. The use of these diluents is even more particularly preferred when about 20% or more of the azithromycin particles have a diameter of about 44 microns or less.

Flavors incorporated in the composition may be chosen from synthetic flavor oils and flavoring aromatics and/or natural oils, extracts from plants leaves, flowers, fruits, and so forth and combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth. The amount of flavoring may depend on a number of factors including the organoleptic effect desired. Generally the flavoring will be present in an amount of from 0.5 to about 3.0 percent by weight based on the total tablet weight, when a flavor is used.

For sachets and powders for suspension, the preferred flavoring comprises a combination of cherry, banana and vanilla flavors as further described in Table XIII of U.S. Pat. No. 5,605,889. The teachings of U.S. Pat. No. 5,605,889, in their entirety, are incorporated herein by reference.

Other excipients and coloring agents may also be added to azithromycin tablets. Coloring agents include, but are not limited to, titanium dioxide and/or dyes suitable for food such as those known as F. D. & C, dyes, aluminum lakes and natural coloring agents such as grape skin extract, beet red powder, beta carotene, annato, carmine, turmeric, paprika, and so forth. A coloring agent is an optional ingredient in the compositions of this invention, but when used will generally be present in an amount up to about 3.5 percent based on the total tablet weight.

Dry blends, that are suitable for direct compression tableting, in the present invention, include up to about 80 weight percent non-dihydrate azithromycin, from about 10 wt % to about 90 wt % binder, from 0 wt % to about 85 wt % diluent, from 2 wt % to about 15 wt % disintegrant; and from about 0.25 wt % to about 10 wt % lubricant.

In a further embodiment, the dry blend contains up to about 80 wt % azithromycin, from about 2 wt % to about 10 wt % disintegrant, from about 0.5 wt % to about 8 wt % lubricant; and from about 0 wt % to about 85 wt % diluent.

To prepare the dry blend, the various components may be weighed, delumped and combined except for the lubricating agent. The mixing may be carried out for a sufficient period of time to produce a homogeneous blend, and then the lubricant may be added. Afterwards, the final mixing may be carried out. The dry blend may be stored for later use or tableted on suitable equipment.

The components of the dry blend, including the azithromycin and at least one excipient, may be combined by blending, mixing, stirring, shaking, tumbling, rolling or by any other methods of combining the formulation components to achieve a homogeneous blend. It is preferable that the azithromycin and excipients are combined under low shear conditions in a suitable apparatus, such as a V-blender, tote blender, double cone blender or any other apparatus capable of functioning under preferred low shear conditions. Lubricant is typically added in the last step.

The invention should not be considered limited to these particular conditions for combining the components and it will be understood, based on this disclosure that the advantageous properties can be achieved through other conditions provided the components retain their basic properties and substantial homogeneity of the blended formulation components of the formulation is otherwise achieved without any significant segregation.

In one embodiment, for preparing the dry blend, the components are weighed and placed, except for the lubricant, into a blending container. Blending is performed for a period of time to produce a homogenous blend using suitable mixing equipment. The dry blend may be passed through a mesh screen to delump the dry blend. The screened dry blend may be returned to the blending container and blended for an additional period of time. The lubricant, such as magnesium stearate, may then be added and the dry blend may be mixed for an additional period of time.

The dry blend is typically free flowing and may be employed in the preparation of a tablet in standard tableting equipment, or stored for later use.

Direct compression tablets provided by this invention are solid, intended for oral use, of uniform appearance and with sufficient mechanical strength to withstand possible damage from storage and transport or a subsequent coating process. In order to prepare a tablet having suitable properties by direct compression methods, the dry blend must have good flow properties, good compactability and other suitable physical characteristics.

The dry blend of the present invention may be employed in the preparation of a tablet using tableting means, such as, standard tableting equipment known in the industry for gravity fed tableting processes and for equipment having means to force feed the pharmaceutical formulation. In one embodiment, the dry blend is used to prepare tablets on a single station tableting press. Tablets comprising azithromycin are useful for the treatment of bacterial and protozoal infections.

In a further aspect of the present invention, an azithromycin tablet is made according to the following steps. First, azithromycin and at least one excipient are blended to form a dry blend. A lubricant may be added to the dry blend during, or subsequent to, the blending of the azithromycin and other excipients. The lubricated dry blend is then compacted to produce a direct compression tablet.

Optionally, the dry blend may be subjected to a delumping process after initial blending. In addition, the lubricated blend may first be subjected to a precompression step on a rotary tablet press prior to the final compression step for tablet formation. The lubricated blend may optionally be force fed into a die prior to compression.

Suitable dry blends, prior to being lubricated, may comprise up to about 80% by weight of azithromycin, from about 10% to about 90% binder, from 0% to about 85% filler, from 2% to about 15% disintegrant.

The lubricated blend may comprise from about 0.25% to about 10% lubricant more preferably from about 0.5% to about 3% of lubricant. The particular amount of lubricant needed will depend, in part, on the particular lubricant chosen. More preferably, a suitable lubricated dry blend comprises from about 30% to about 60% azithromycin.

In one embodiment, the direct compression tablet may comprise an amount of lubricant that is greater than about 1% by weight, based on the tablet weight, and less than about 6% by weight, based on the tablet weight. In a further embodiment, the direct compression tablet may comprise an amount of lubricant that is greater than or equal to about 2% by weight, based on the tablet weight, and less than or equal to about 5% by weight, based on the tablet weight. In an even further embodiment, the direct compression tablet may comprise an amount of lubricant that is greater than or equal to about 3% by weight, based on the tablet weight, and less than or equal to about 5% by weight, based on the tablet weight.

In one embodiment, the direct compression tablet may comprise an amount of glidant that is less than about 3% by weight, based on the tablet weight. In a further embodiment, the direct compression tablet may comprise an amount of glidant that is less than about 1% by weight, based on the tablet weight. In an even further embodiment, the tablet may comprise an amount of glidant that is less than about 0.5% by weight, based on the weight of the glidant. Suitable glidants include magnesium trisilicate, powdered cellulose, starch, talc, tribasic calcium phosphate, stearate salts and colloidal silicon dioxide. Most preferred glidants are talc, magnesium stearate and colloidal silicon dioxide.

Typical compacting techniques for the preparation of a tablet by direct compression utilize a piston like device with three stages in each cycle 1) filling (adding the constituents of the tablet to the compression chamber) 2) compaction (forming the tablet) and 3) ejection (removing the tablet). The cycle is then repeated. A representative tablet press is a Manesty Express 20 rotary press, manufactured by Manesty Machines Ltd., Liverpool, England, and many others are available. The equipment may be gravity fed or it may utilize means to force feed the lubricated blend into the die. One common method is to use a feed frame, which is equipped with moving paddles to aid in feeding the blend into the die cavities. It should be understood that compacting methods and techniques as described in the present specification are not limited to any particular equipment.

In one embodiment, a high speed tablet press may be used. In a further embodiment, a single station tableting press may be used. Flow of the blend on high speed tablet presses is very important to good weight control of the tablet. The use of a force feeder often improves tablet weight control for poorer flowing blends. Another common feature of high speed tablet presses is the ability to use precompression. Precompression taps the blend when the die is full with blend before the final compression step forms the tablet.

The tablets may be any shape as long as the tablet is in a form that it may be administered orally and is not prone to capping or exceeds the desired friability. The tablets may be round, oblong, thick or thin, large or small in diameter, flat or convex, scored or unscored, and imprinted. In one embodiment, the tablets are round, in a further embodiment, the tablets are modified oval or modified capsule shaped.

In one embodiment, the tablet may be a modified capsule shape containing about 250 mgA, about 450 mg total weight. In one embodiment, the dimensions of the aforementioned tablet are 0.26"×0.53". In a further embodiment, the tablet may be a modified oval shape containing about 500 mgA, about 900 mg total weight. In one embodiment, the dimensions of the tablet are 0.33"×0.67". In an even further embodiment, the tablet may be a modified oval shape containing about 600 mgA, about 1070 mg total weight. In one embodiment, the dimensions of the aforementioned tablet are 0.41"×0.75". A reference to tablet shapes can be found in FIG. 25, page 51 of the *Tableting Specification Manual*, fourth edition, published by the American Pharmaceutical Association, Washington, D.C., 1995; incorporated herein by reference in its entirety.

In one embodiment, the direct compression tablet may comprise an amount of azithromycin equivalent to about 250 mgA. In a further embodiment the direct compression tablet may comprise an amount of azithromycin equivalent to about 500 mgA. In an even further embodiment the direct compression tablet may comprise an amount of azithromycin equivalent to about 600 mgA.

The tablets prepared from the pharmaceutical formulation of the present invention exhibit acceptable physical characteristics including good friability and hardness. The resistance of a tablet to chipping, abrasion or breakage under conditions of storage and transportation depends on its hardness and friability.

Friability is a standard test known to one skilled in the art. Friability is measured under standardized conditions by weighing out a certain number of tablets (generally 20 tablets or less), placing them in a rotating Plexiglas drum in which they are lifted during replicate revolutions by a radial lever, and then dropped approximately 8 inches. After replicate revolutions (typically 100 revolutions at 25 rpm), the tablets are reweighed and the percentage of formulation abraded or chipped is calculated. The friability of the tablets, of the present invention, is preferably in the range of about 0% to 3%, and values about 1%, or less, are considered acceptable for most drug and food tablet contexts. Friability which approaches 0% is particularly preferred.

If desired, the tablet may be coated. The reasons for coating a tablet may include masking the taste of the drug, making tablets easier to swallow, protection against chipping during packaging, a barrier for moisture or light to improve product stability, and enhance product appearance or recognition.

The coating process may include the use of a coating solution or suspension, usually aqueous that has acceptable viscosity for spraying and properties for it to adhere to the surface of the tablet when applied. During the coating process, the coating solution or suspension is atomized into fine droplets that come into contact with the tablet. As the droplets dry, a film is formed on the tablet which is the coating. There are several types of coating equipment used to coat tablets. One type is the pan coater in which tablets are rotated in a pan and coating solution is applied to the tablets as tablets tumble in the pan. Another coating process involves suspending the tablets in a column of air while the coating solution is sprayed onto the tablet (fluid bed process). One example of this is the Wurster column coating process. The tablet may be coated by any known process and the manner of application is not limited to any particular equipment.

The tablet coating(s) may be a white or colored Opadry® (Colorcon, West Point Pa.) suspension or a clear Opadry® solution. Alternatively a typical coating formulation would consist of a film forming polymer(s) such as hydroxypropyl methylcellulose (HPMC), hydroxypropyl cellulose (HPC), polyvinyl pyrrolidone (PVP) with additional ingredients such as plasticizers, opacifiers, colorants, and antioxidants. Sugar coating could also be used.

The dry blends, of the present invention, are suitable for use in the preparation of a free flowing pharmaceutical formulation. The formulation may be useful, for example, as a preblend and for use in dosage forms such as capsules, sachets and powders for suspension.

Alternatively, pharmaceutical formulations comprising greater than about 80% by weight of azithromycin, and having the good flow properties described, may be used to prepare other dosage forms, such as capsules. In addition, it might be advantageous to store bulk azithromycin and excipients separately prior to a direct compression tableting operation.

Azithromycin formulations as defined in this aspect of the invention may contain bulk drug by itself or bulk drug with one or more excipients such as binders, diluents, disintegrants, lubricants, fillers, carriers, and the like, as set forth above.

The formulation may also be used in other applications, including but not limited to filling a capsule dosage form or any other process that requires good flow in the pharmaceutical formulation.

The pharmaceutical compositions of the present invention may be used for the treatment of bacterial or protozoal infections. The term "treatment", as used herein, unless otherwise indicated, means the treatment or prevention of a bacterial or protozoal infection, including curing, reducing the symptoms of or slowing the progress of said infection.

As used herein, unless otherwise indicated, the term "bacterial infection(s)" or "Protozoal infection(s)" includes bacterial infections and protozoal infections that occur in mammals, fish and birds as well as disorders related to bacterial infections and protozoal infections that may be treated or prevented by administering antibiotics such as the compound of the present invention. Such bacterial infections and protozoal infections and disorders related to such infections include, but are not limited to, the following: pneumonia, otitis media, sinusitis, bronchitis, tonsillitis, and mastoiditis related to infection by *Streptococcus pneumoniae, Haemophilus influenzae, Moraxella catarrhalis, Staphylococcus aureus*, or *Peptostreptococcus* spp.; pharyngitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal Groups C-F (minute-colony streptococci), *viridans streptococci, Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Neisseria gonorroeae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp.; odontogenic infection related to infection by *viridans streptococci*; persistent cough related to infection by *Bordetella pertussis*; gas gangrene related to infection by *Clostridium perfringens* or *Bacteroides* spp.; and atherosclerosis related to infection by *Helicobacter pylori* or *Chlamydia pneumoniae*. Bacterial infections and protozoal infections and disorders related to such infections that may be treated or prevented in animals include, but are not limited to, the following: bovine respiratory disease related to infection by *P. haem., P. multocida, Mycoplasma bovis*, or *Bordetella* spp.; cow enteric disease related to infection by *E. coli* or protozoa (i.e., *coccidia, cryptosporidia*, etc.); dairy cow mastitis related to infection by *Staph. aureus, Strep. uberis, Strep. agalactiae, Strep. dysgalactiae, Klebsiella* spp., *Corynebacterium*, or *Enterococcus* spp.; swine respiratory disease related to infection by *A. pleuro., P. multocida*, or *Mycoplasma* spp.; swine enteric disease related to infection by *E. coli, Lawsonia intracellularis, Salmonella*, or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius, coagulase neg. Staph.* or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas*, or *Prevotella*. Other conditions that may be treated by the compounds and preparations of the present invention include malaria and atherosclerosis. Other bacterial infections and protozoal infections and disorders related to such infections that may be treated or prevented in accord with the method and compositions of the present invention are referred to in J. P. Sanford et al., "The Sanford Guide To Antimicrobial Therapy," 26th Edition, (Antimicrobial Therapy, Inc., 1996).

The term "effective amount" means the amount of azithromycin which, when administered in—the present invention prevents the onset of, alleviates the symptoms of, stops the progression of, or eliminates a bacterial or protozoal infection in a mammal.

The term "mammal" is an individual animal that is a member of the taxonomic class Mammalia. The class Mammalia includes, for example, humans, monkeys, chimpanzees, gorillas, cattle, swine, horses, sheep, dogs, cats, mice and rats.

In the present invention, the preferred mammal is a human.

Typically, azithromycin, is administered in dosage amounts ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. The preferred dosage amount is from about 2 mg/kg/day to about 50 mg/kg/day.

The azithromycin may be administered orally, or by other known means for administering azithromycin.

Although the foregoing invention has been described in some detail for purposes of illustration, it will be readily apparent to one skilled in the art that changes and modifications may be made without departing from the scope of the invention described herein.

Exemplification

The present invention will be further illustrated by means of the following examples. It is to be understood, however, that the invention is not meant to be limited to the details described therein.

In the following examples, particle size distribution was determined using a Malvern Mastersizer S (Malvern Instruments, Worcestershire, UK) with a MS-1-Small Volume Sample Dispersion Unit. This unit allowed for particle size analysis through a wet sample dispersion step and subsequent particle size measurements using laser diffraction. To determine the particle size, 60 to 75 milliliters of purified water were added to the small volume sample dispersion unit and allowed to stir for about 15 seconds, followed by a 5000 sweep background count. Immediately thereafter, azithromycin bulk was added to this liquid until an obscuration value of 15–25% was achieved, and measurement of the particle size was accomplished using 5000 sweeps as exhibited by FIG. 1.

Carr's Compressibility Index of the azithromycin bulk was measured by taking an initial density of a 15 gram sample in a 100 ml graduated cylinder. The sample was tapped 2000 times on a VanKel Tap Density Tester (Model 50-1200, Edison, N.J.) and the tapped density of the 15 gram sample in the 100 ml graduated cylinder was taken. The procedure is described in *Int. J. Pharm. Tech. & Prod. Mfr.*, 6(3) 10–16, 1985.

Internal angle of friction of the bulk drug was measured by the method described in "Some Measurements of Friction in Simple Powder Beds", Hiestand, E. N. and Wilcox, C. J. (J. Pharm. Sci. 57 (1968) 1421).

The shear cell consisted of a layer of powder between two parallel flat surfaces. The lower surface was fixed and formed the base, while the upper surface (sled) was attached to an actuator which provided a force in a linear direction parallel to the plane of the surfaces. Another force was applied on top of the sled using weights of known mass. For each sample, the test was performed several times using a different weight on the sled for each test. The force, or resulting shear stress, required to pull the sled across the powder layer increased as the weight on the sled, or resulting normal stress was increased. When the powder bed yielded during shear, it is said to have failed. This condition represented incipient flow and occurred when the amount of force needed to move the sled stopped increasing. The data at several normal stress levels were plotted as the shear vs. normal stress at failure. This plot is known as the yield locus, while the angle between the yield locus and the abscissa is known as the Angle of Internal Friction.

The following excipients' trade names are referenced in the examples:
Lactose (316 Fast Flo®) was obtained from Foremost Farms, Baraboo, Wis.
Microcrystalline cellulose (Avicel® PH-200) was obtained from FMC Biopolymer, Philadelphia, Pa.
Croscarmellose sodium (Ac-Di-Sol®) was obtained from FMC Biopolymer, Philadelphia, Pa.
Magnesium stearate was obtained from Mallinckrodt, Inc., St. Louis, Mo.
Colloidal silicon dioxide was obtained from Cabot Corporation, Tuscola, Ill.
Talc was obtained from Whitaker, Clark & Daniels Inc., South Plainfield, N.J.

Further, in the following examples, the following drug lots were evaluated:
Lot 1: Form N, unmilled
Lot 2: Form M, unmilled
Lot 3: Form A, unmilled
Lot 4: Form G, unmilled
Lot 5: Form A, milled on Fitzmill with 0.027" screen, hammers, low speed
Lot 6: Form A, milled on Fitzmill no screen, hammers, high speed
Lot 7: Form A, milled on Fitzmill, 0.027" screen, knives, medium speed
Lot 8: Form A, milled on Fitzmill, 0.020" screen, knives, high speed
Lot 9: Form M, milled on Fitzmill, 0.033" rasping screen, bar rotor, low speed
Lot 10: Form F, unmilled
Lot 11: Form J, unmilled

EXAMPLE 1

Indices of Tableting Performance

Indices of tableting performance, for several azithromycin forms, were assessed to identify any mechanical deficiencies or attributes that may affect the ability to develop a direct compression tablet formulation of azithromycin. This assessment was performed in accordance with the procedures described in "Indices of Tableting Performance" H. E. N. Hiestand and D. P. Smith, Powder Technology 38 [1984] pp. 145–159.

More specifically, the Brittle Fracture Index, BFI, was calculated from the ratio of a material's regular tensile strength to its compromised tensile strength. Strain Index, SI, was determined from the dynamic indentation hardness test. Worst Case Bonding Index was determined by assessing the extent of particle bonding remaining after decompression assuming a very short compression dwell time and a plastic mechanism of particle separation during decompression.

Bulk azithromycin lots 1, 2, 4, 7, 10 and 11 are different crystalline forms, respectively, forms N, M, G, A, F and J. Lots 1, 2 and 4 were milled with a Fitzmill (Model JT, The Fitzpatrick Co., Elmhurst, Ill.) using a 0.027" screen and knives at high speed in an attempt to match the smaller particle size of Lot 7. Lots 10 and 11 were evaluated as is due to their relatively small particle sizes.

The results of these assessments are provided, below, in Table 1.

TABLE 1

Indices of Tableting Performance

| Lot # | Brittle Fracture Index (BFI) | Worst Case Bonding Index ($BL_w$) × $10^2$ | Strain Index (SI) | Tensile Strength Mpa |
|---|---|---|---|---|
| #1 Form N | 0.05 | 0.7 | 0.0044 | 0.75 |
| #2 Form M | 0.10 | 1.0 | 0.0048 | 0.79 |
| #4 Form G | ND | 0.8 | 0.0043 | 1.03 |
| #7 Form A | 0.10 | 0.9 | 0.0044 | 0.99 |
| #10 Form F | 0.37 | 0.9 | 0.0041 | 1.62 |
| #11 Form J | 0.11 | 0.7 | 0.0043 | 0.69 |

ND = not determined

As shown above, the tableting indices were similar for Lots 1, 2, 4, 7 and 11 (Forms N, M, G, A and J). The data suggests that the primary deficiencies of these materials, in forming tablets by direct compression, are their low to moderate tensile strengths. This may be manifested as low tablet hardness values. Further, the brittle fracture indices indicate that bonds formed during compression will more likely survive decompression when the tablet is ejected from the die. Differences between these lots were not significant. Thus, these lots would likely have a similar probability of forming a robust direct compression tablet formulation.

Lot 10 (form F), however, appeared to have significantly different mechanical properties. It has a higher tensile strength value indicative of forming stronger bonds. The flow properties of Lot 10, however, were similar to the other lots having a similar particle size distribution.

In general, a direct compression tablet may be feasible with high drug loading (~60%) if low brittleness, and good bonding excipients were used.

EXAMPLE 2

Particle Size Effect

The impact of azithromycin particle size on a direct compression tablet was evaluated as follows.

Using various lots of azithromycin, direct compression tablets were prepared from a dry blend of 59.3 wt % azithromycin, 26.9 wt % microcrystalline cellulose as the binder, 8.9 wt % lactose as the diluent, 2.0 wt % croscarmellose sodium as the disintegrant, and 2.9 wt % magnesium stearate as the lubricant.

The ingredients were weighed (except for the magnesium stearate), combined and blended in a low shear blender for 30 minutes. The blend was passed through a U.S. standard No. 20 or No. 25 mesh screen to delump the blend. The screened blend was returned to the blender and blended for an additional 30 minutes. Prior to the addition of the magnesium stearate, the initial and tapped densities of the blend were determined from which a Carr's Compressibility Index for flow was calculated for the blend. Magnesium stearate was then added to the blend, after which it was blended for an additional five minutes.

The dry blends were compacted on a single station tablet press Manesty F-press (Manesty, Liverpool, United Kingdom) with 0.262"×0.531" modified capsule shaped tooling. The target tablet weight was 450 milligrams. The tablets were tested for hardness (kP scale), using a Schleuniger hardness tablet tester (Dr. Schleuniger Pharmatron AG, Solothurn, Switzerland), and for friability (100 rotations/4 minutes) using a Vanderkamp Friabulator Tablet Tester (Vankel, Cary, N.C., US). The test results are provided in Table 2.

TABLE 2

| Run and Lot # | Angle of Internal Friction (°) | Dry Blend Carr's Index (%) | Average Tablet Weight mg (% CV) | Avg. Tablet Hardness (kP) | Tablet Friability (%) |
|---|---|---|---|---|---|
| 1 | ND | 19 | 451.5 (0.67%, n = 10) | 6.6 (n = 10) | 0.6 (n = 5) |
| 2 | ND | 25 | 445.1 (0.32%, n = 3) | 6.7 (n = 3) | ND |
| 3 | 31.0 | 25 | 455.3 (0.21%, n = 5) | 6.2 (n = 5) | 1.1 (n = 5) |
| 4 | 30.5 | 30 | 442.4 (0.50%, n = 10) | 10.1 (n = 10) | 0.52 (n = 10) |
| 5 | 31.6 | 30 | 455 (0.36%, n = 10) | 8.6 (n = 10) | 0.32 (n = 5) |
| 6 | 32.6 | 30 | 452.5 (0.90%, n = 10) | 4.1 (n = 10) | 1.8 (n = 10) |
| 7 | 34.5 | 34 | 450.8 (2.06%, n = 5) | 12.5 (n = 5) | 3.67 (n = 5) |
| 8 | ND | 37 | No tablets | N/A | N/A |
| 9 | ND | 46 | No tablets | N/A | N/A |
| 10 | ND | 34 | No tablets | N/A | N/A |

ND = Not Determined

Evaluation of the dry blends showed that the unmilled bulk drug (Runs 1–4) resulted in acceptable flowing blends having a Carr's Compressibility Index from 19 to 30 on the tablet press, and tablets with acceptable weight control, hardness and friability. The less aggressively milled bulk drug lots (Runs 5–6) also resulted in acceptable flowing blends on the tablet press.

As shown in Table 2, more aggressively milled bulk drug lots (Runs 8 and 9) and unmilled bulk drug having a small particle size distribution (Run 10) produced poorer flowing blends (Carr's Index of 34 to 46) such that tablets could not be compacted on the Manesty F-press.

A compaction simulator was then used to compress blends containing azithromycin from Lots 7, 8, 9 and 10. The compaction simulator was designed as a single station tablet press in which the compression dwell time can be adjusted to simulate different types of tablet presses. In addition, the compaction simulator was equipped with a mechanical agitator to assist in filling the tablet die with dry blends to obtain a consistent tablet weight.

As shown in Runs 11, 12, 13A, 13B, 14A and 14B of Table 2A, poor flowing blends that resulted in unacceptable tablets on the Manesty F-press became acceptable tablets when compressed on the compaction simulator.

TABLE 2A

| Run | Drug Lot | Carr's Index of dry blend (%) | Applied Upper Compression Force (kN) | Average Tablet Weight Mg (% CV) | Average Tablet Hardness (kP) | Tablet Friability (%) |
|---|---|---|---|---|---|---|
| 11 | 7 | 34 | 5.1 | 457.2 (2.53%, n = 5) | 9.3 (n = 5) | 0.32 (n = 5) |
| 12 | 8 | 37 | 4.0 | 439.8 (1.08%, n = 5) | 6.4 (n = 5) | 0.73 (n = 5) |
| 13A | 9 | 46 | 4.6 | 428.7 (1.15%, n = 10) | 10.6 (n = 10) | 0.35 (n = 10) |
| 13B | 9 | 46 | 5.5 | 426.9 (1.44%, n = 10) | 11.9 (n = 10) | 0.32 (n = 10) |
| 14A | 10 | 34 | 4.2 | 444.9 (0.90%, n = 5) | 10.4 (n = 5) | 0.38 (n = 10) |
| 14B | 10 | 34 | 5.7 | 456.2 (0.62%, n = 5) | 14.1 (n = 5) | 0.41 (n = 10) |

EXAMPLE 3

Drug Loading Effects

The effects of drug loading on the tableting properties of azithromycin direct compression tablets were evaluated as follows. Azithromycin tablets were evaluated with low, medium and high drug loadings. The same manufacturing and testing procedures as set forth in Example 2 were used.

Pharmaceutical formulations having the following drug loadings were used (percentages are given as % weight):

|  | Drug Loading | | |
|---|---|---|---|
|  | ~60% | ~45% | ~30% |
| Azithromycin | 59.3% | 44.5% | 29.7% |
| Microcrystalline Cellulose | 26.9% | 38.0% | 49.2% |
| Lactose | 8.9% | 12.6% | 16.2% |
| Croscarmellose Sodium | 2.0% | 2.0% | 2.0% |
| Magnesium Stearate | 2.9% | 2.9% | 2.9%. |

Runs 1, 2, 3, 4, 5 and 6, in Table 3, were conducted on a Manesty F-press. The same bulk drug, Lot 8 was used for Runs 1–3, Lot 10 for Runs 4–5, and Lot 11 for Run 6. Runs 7, 8, 9, 10, 11, and 12 in Table 3A were conducted on the compaction simulator using Lot 8, Lot 10, and Lot 11.

Initial evaluation using ~60% drug loading of the milled bulk drug Lot 8 and unmilled Lot 10 resulted in poor flowing blends (Carr's Index of 37 and 34 respectively) and poor tablets on the Manesty F-press as shown in Table 2 (Runs 3 and 5). However, low drug loading (~30%) did improve the flow of the blend and properties as shown in Table 3.

TABLE 3

| Run | Drug Lot | Carr's Index (%) | Drug Load (%) | Average Tablet Weight mg (% CV) | Average Tablet Hardness (kP) | Tablet Friability (%) |
|---|---|---|---|---|---|---|
| 1 | 8 | 33 | 30 | 449.7 (0.56%, n = 10) | 7.5 (max) (n = 5) | 0.25 (n = 5) |
| 2 | 8 | 39 | 45 | 457.7 (3.38%, n = 8) | 3.7 (max) (n = 4) | 2.02 (n = 4) |
| 3 | 8 | 37 | 60 | No tablets | No tablets | No tablets |
| 4A | 10 | 28 | 30 | 441.70 (0.95%, n = 10) | 11.5 (n = 10) | 0.27 |
| 4B | 10 | 28 | 30 | 446.9 (0.89%, n = 10) | 20.2 (n = 10) | 0.31 |
| 5 | 10 | 34 | 60 | No tablets | No tablets | No tablets |
| 6A | 11 | 33 | 30 | 450.2 (0.36%, n = 5) | 10.6 (n = 2) | 0.20% (n = 3) |
| 6B | 11 | 33 | 30 | 449.0 (0.47%, n = 5) | 16.4 (n = 2) | 0.44% (n = 5) |

TABLE 3A

| Run/Lot % Drug Loading | Carr's Index (%) | Applied Upper Compression Force (kN) | Average Tablet Weight mg (% CV) | Average Tablet Hardness (kP) | Tablet Friability (%) |
|---|---|---|---|---|---|
| 7/8 30% | 33 | 7.2 | 459.6 (0.62%, n = 20) | 12.9 (n = 10) | 0.21 |
| 8/8 45% | 39 | 5.8 | 455.2 (0.15%, n = 15) | 10.5 (n = 5) | 0.13 (n = 5) |
| 9/8 60% | 37 | 4 | 439.8 (1.08%, n = 5) | 6.4 (n = 5) | 0.73 (n = 5) |
| 10/10 60% | 34 | 4.2 | 444.9 (0.90%, n = 5) | 10.4 (n = 5) | 0.38 (n = 10) |
| 11/11 30% | 33 | 6.8 | 452.0 (n = 1) | 18.3 (n = 1) | ND |
| 12/11 30% | 33 | 4.4 | 451.0 (0.44%, n = 5) | 12.3 (n = 5) | 0.35 (n = 5) |

ND = Not Determined

As shown, above, in Table 3A, tablets made on the compaction simulator were significantly improved in hardness and friability at medium drug load when compared to high drug load when using Lot 8. At low drug loading with Lot 8 or Lot 11, tablets with hardness greater than 12 kP were achieved using the compaction simulator. Tablets could also be made with Lot 8 or Lot 10 at the high drug loading using the compaction simulator. Flow is not a critical parameter for the compaction simulator since it uses a mechanical agitator to force the blend into the die.

EXAMPLE 4

Effect of Lubricant

The effect of lubricant levels on the tableting properties of the azithromycin direct compression tablet were evaluated as follows. Direct compression tablet formulations, containing high an low levels of magnesium stearate, as a lubricant, were prepared. The high level lubricant formulation contained 59.3 wt % azithromycin, 26.9 wt % microcrystalline cellulose, 8.9 wt % lactose, 2.0 wt % croscarmellose sodium, and 2.9 wt % magnesium stearate. The low level lubricant formulation contained 59.3 wt % azithromycin, 28.3 wt % microcrystalline cellulose, 9.4 wt % lactose, 2.0 wt % croscarmellose sodium, and 1.0 wt % magnesium stearate.

Azithromycin lot 8 was used for the two lubricant level formulations. The same manufacturing and testing procedures, from Example 2, were used herein.

Evaluation of this bulk drug lot with lubricant at about 3% resulted in a poor flowing blend (Carr's Compressibility Index of 37). Tablets could not be made on the Manesty F-press as shown in Table 4. With the lubricant level at 1%, the blend was also poor flowing (Carr's Compressibility Index of 47) and only unacceptable tablets were made on the F-press with excessive build up of the material on the punches. The tablets were very soft with unacceptable low tablet weight (target tablet weight is 450 mg) and poor weight control (% Cv=5.1%).

TABLE 4

| Run | Carr's Index (Dry Blend) (%) | Lubricant (%) | Average Tablet Weight mg (% CV) | Average Tablet Hardness (kP) | Tablet Friability (%) |
|---|---|---|---|---|---|
| 1 | 37 | 3 | No tablet | No tablet | No tablet |
| 2 | 47 | 1 | 418.3 (5.1%, n = 10) | 3.3 (n = 5) | 2.5 |

As shown in Runs 3 and 4 in Table 4A, poor flowing blends that resulted in unacceptable tablets on the Manesty F-press became acceptable tablets when compressed on the compaction simulator. Flow is not a critical parameter for the compaction simulator since it uses a mechanical agitator to force the blend into the die. Better tablet friability was achieved with the 1% lubricant level blend compressed on the compaction simulator (Run 4).

TABLE 4A

| Run | Carr's Index (Dry Blend) (%) | Lubricant (%) | Applied Upper Compression Force (kN) | Average Tablet Weight mg (% CV) | Average Tablet Hardness (kP) | Tablet Friability (%) |
| --- | --- | --- | --- | --- | --- | --- |
| 3 | 37 | 3 | 4.0 | 439.8 (1.07%, n = 5) | 6.4 (n = 5) | 0.73 (n = 5) |
| 4 | 47 | 1 | 4.2 | 462.8 (0.69%, n = 20) | 5.8 (n = 10) | 0.15 |

EXAMPLE 5

Effect of Glidant

The effect of glidant on tableting properties of the azithromycin direct compression tablet were evaluated as follows. Typically, glidants are added into pharmaceutical formulations to improve flow. As shown in this example, addition of glidants into the formulation can improve flow.

Azithromycin direct compression tablets were prepared with glidants to evaluate the effects on the direct compression tablet. The same bulk drug, lot number 6, was used for all glidant formulations. The same manufacturing and tablet testing procedures from Example 2 were used in this example. Runs 1, 2, 3 and 4 were conducted on the Manesty F-press.

The following pharmaceutical formulations were prepared:

| | Run # | | | |
| --- | --- | --- | --- | --- |
| | 1 | 2 | 3 | 4 |
| Glidant Formulation | wt % | | | |
| Azithromycin | 59.3 | 59.3 | 59.3 | 59.3 |
| Microcrystalline cellulose | 26.8 | 26.8 | 26.7 | 26.9 |
| Lactose | 8.9 | 8.9 | 8.8 | 8.9 |
| Croscarmellose Sodium | 2.0 | 2.0 | 2.0 | 2.0 |
| Colloidal Silicon Dioxide | 0.1 | — | 0.3 | — |
| Talc | — | 0.1 | — | — |
| Magnesium Stearate | 2.9 | 2.9 | 2.9 | 2.9 |

TABLE 5

| Run | Carr's Index (Dry Blend) (%) | Glidant | Tablet weight mg (% CV) | Tablet hardness (kP) | Tablet Friability % |
| --- | --- | --- | --- | --- | --- |
| 1 | 25 | 0.10% silicon dioxide | 455.5 (0.4%, n = 5) | 4.6 (n = 5) | 2.29 (n = 7) |
| 2 | 27 | 0.10% talc | 449.5 (1.2%, n = 5) | 3.6 (n = 5) | 2.68 (n = 7) |
| 3 | 28 | 0.25% silicon dioxide | 445.2 (1.06%, n = 10) | 4.7 (n = 10) | Tablets capped |
| 4 | 30 | No glidant | 452.5 (0.9%, n = 10) | 4.1 (n = 10) | 1.8 (n = 10) |

Initial evaluation of the bulk drug lot 6 without glidant, as shown in Table 5, resulted in acceptable blend flow (Carr's Compressibility Index of 30) on the Manesty F-press. The addition of 0.1% silicon dioxide (Run 1) improved the flow as measured by Carr's Compressibility Index and the weight uniformity as shown by the lower weight % CV.

EXAMPLE 6

Effect of Sizing

The effect of sieving the bulk drug to selectively remove fines from the bulk azithromycin lot follows.

Lot 8 was screened through a #200 mesh screen using a vibrating sieve analyzer (Endecott's Octagon 200 test sieve shaker, Endecott, London, England) for 20 minutes at an amplitude setting of 8. The drug retained on the #200 mesh screen was sieved again using the same screening process. The drug retained on the #200 mesh screen (screened twice) was used in the following direct compression formulation. The same manufacturing and testing procedures from Example 2 were used in this example. The direct compression tablets had the following composition, by weight:

| | |
| --- | --- |
| Azithromycin | 59.3% |
| Microcrystalline Cellulose | 26.9% |
| Lactose | 8.9% |
| Croscarmellose Sodium | 2.0% |
| Magnesium Stearate | 2.9% |

A better flowing blend (Carr's Compressibility Index of 29) was produced from the sieved bulk drug lot. When unsieved Lot 8 was used, the blend was poor flowing (Carr's Compressibility Index of 37) and tablets could not be made (Run 1) on the Manesty F-press as shown in Table 6. Using the sieved Lot 8 (Runs 2a and 2b), acceptably hard tablets were produced. Runs 2a and 2b were performed with different upper punch compression settings. Run 2b had a higher setting resulting in greater compression. The target tablet weight of 450 mg was achieved with good to excellent weight control.

TABLE 6

| Run | Carr's Index (Dry Blend) (%) | Bulk Drug Lot Pretreatment | Average Tablet Weight mg (% CV) | Average Tablet Hardness (kP) |
|---|---|---|---|---|
| 1 | 37 | None, unsieved | No tablet | No tablet |
| 2a | 29 | Screened twice #200 mesh | 448.4 (1.48%, n = 5) | 5.6 (n = 5) |
| 2b | 29 | Screened twice #200 mesh | 449.2 (0.06%, n = 5) | 8.3 (n = 5) |

We claim:

1. A dry blend, used for forming azithromycin tablets by direct compression, comprising:
   (a) about 1–80%, by weight non-dihydrate azithromycin; and
   (b) at least one pharmaceutically acceptable excipient; wherein the Carr's Compressibility Index, of the dry blend, is less than about 34%; wherein said non-dihydrate azithromycin is azithromycin monohydrate hemi-isopropanol solvate or azithromycin monohydrate hemi-n-propanol solvate.

2. A dry blend of claim 1 further comprising from about 0.25–10% by weight, of a lubricant; wherein the non-dihydrate azithromycin is azithromycin monohydrate hemi-isopropanol solvate.

3. A dry blend of claim 1 wherein the non-dihydrate azithromycin is non-granulated.

4. A dry blend of claim 1 further comprising about 0.1–85%, by weight, of a diluent.

5. A dry blend of claim 4 wherein said diluent is from 20–70%, by weight.

6. A dry blend of claim 5 wherein the diluent is selected from a group consisting of anhydrous lactose, lactose monohydrate, microcrystalline cellulose, silicified microcrystalline cellulose, dextrate, mannitol, sorbitol and dihydrated dibasic calcium phosphate.

7. A dry blend of claim 5 wherein the Carr's Compressibility Index, of the dry blend, is less than about 31%.

8. A dry blend of claim 5 wherein the Carr's Compressibility Index, of the dry blend, is less than about 28%.

9. A dry blend of claim 1 further comprising from about 2–15%, by weight, of a disintegrant.

10. A dry blend of claim 9 further comprising:
    (a) about 2–10%, by weight, of the disintegrant; and
    (b) about 0.5–8%, by weight, of a lubricant.

11. A dry blend of claim 1 wherein said lubricant is from about 0.5–3%, by weight.

12. A dry blend of claim 1 wherein said lubricant is selected from the group consisting of magnesium stearate, calcium stearate, zinc stearate and a mixture of magnesium stearate and sodium lauryl sulfate.

13. A dry blend of claim 1 further comprising a glidant.

14. A dry blend of claim 13 wherein the glidant is selected from the group consisting of magnesium trisilicate, powdered cellulose, starch, talc, tribasic calcium phosphate, stearate salts and colloidal silicon dioxide.

15. A dry blend of claim 14 wherein the glidant is selected from the group consisting of talc, magnesium stearate and colloidal silicon dioxide.

16. A dry blend of claim 1 comprising:
    (a) about 30–80%, by weight, non-dihydrate azithromycin;
    (b) about 10–90%, by weight, binder;
    (c) about 0–85%, by weight, diluent;
    (d) about 2–15%, by weight, disintegrant; and
    (e) 0.25–10%, by weight, lubricant.

17. A dry blend of claim 16 comprising:
    (a) about 2–10%, by weight, disintegrant; and
    (b) 0.5–8%, by weight, lubricant.

18. A dry blend of claim 1 wherein the non-dihydrate azithromycin is azithromycin monohydrate hemi-n-isopropanol solvate.

19. A dry blend of claim 1 wherein the Carr's Compressibility Index, of the dry blend, is less than about 31%.

20. A dry blend of claim 1 wherein the Carr's Compressibility Index, of the dry blend, is less than about 28%.

21. A dry blend of claim 1 wherein the internal angle of friction, of the dry blend, is less than about 34°.

22. A dry blend of claim 1 wherein the internal angle of friction, of the dry blend, is less than about 31°.

23. A dry blend of claim 1 wherein less than about 6% of the total azithromycin particles, by volume as measured by the Malvern method, have a diameter of 16 μm or less.

24. A dry blend of claim 1 wherein less than about 20% of the total azithromycin particles, by volume as measured by the Malvern method, have a diameter of 44 μm or less.

25. A dry blend of claim 24 wherein less than about 14% of the total azithromycin particles, by volume as measured by the Malvern method, have a diameter of 44 μm or less.

26. A dry blend of claim 1 wherein less than about 60% of the total azithromycin particles, by volume as measured by the Malvern method, have a diameter of 105 μm or less.

27. A dry blend of claim 26 wherein less than about 50% of the total azithromycin particles, by volume as measured by the Malvern method, have a diameter of 105 μm or less.

28. A dry blend of claim 25 wherein less than about 27% of the total azithromycin particles, by volume as measured by the Malvern method, have a diameter of 74 μm or less.

29. A dry blend of claim 1 wherein, by volume as measured by the Malvern method,
    (a) less than about 6% of the azithromycin particles have a diameter of about 16 μm or less; and
    (b) less than about 20% of the azithromycin particles have a diameter of about 44 μm or less.

30. A dry blend of claim 29 wherein less than about 14% of the total azithromycin particles, by volume as measured by the Malvern method, have a diameter of 44 μm or less.

31. A dry blend of claim 1 wherein, by volume as measured by the Malvern method,
    (a) less than about 6% of the azithromycin particles have a diameter of about 16 μm or less;
    (b) less than about 20% of the azithromycin particles have a diameter of about 44 μm or less; and
    (c) less than about 27% of the azithromycin particles have a diameter of about 74 μm or less.

32. A dry blend of claim 31 wherein less than about 14% of the total azithromycin particles, by volume as measured by the Malvern method, have a diameter of 44 μm or less.

33. A dry blend of claim 1 wherein, by volume as measured by the Malvern method,
    (a) less than about 6% of the azithromycin particles have a diameter of about 16 μm or less;
    (b) less than about 20% of the azithromycin particles have a diameter of about 44 μm or less;
    (c) less than about 27% of the azithromycin particles have a diameter of about 74 μm or less; and (d) less than about 60% of the azithromycin particles have a diameter of about 105 μm or less.

34. A dry blend of claim 33 wherein less than about 14% of the total azithromycin particles, by volume as measured by the Malvern method, have a diameter of 44 μm or less.

35. A dry blend of claim 33 wherein, by volume as measured by the Malvern method,
(a) less than about 14% of the azithromycin particles have a diameter of 44 μm or less; and
(b) less than about 50% of the azithromycin particles have a diameter of 105 μm or less.

36. A dry blend, used for forming azithromycin tablets by direct compression, comprising:

(a) azithromycin monohydrate hemi-isopropanol solvate or azithromycin monohydrate hemi-n-propanol solvate; and (b) at least one pharmaceutically acceptable excipient.

* * * * *